US010653626B2

(12) United States Patent
Lu et al.

(10) Patent No.: US 10,653,626 B2
(45) Date of Patent: May 19, 2020

(54) POWDER FOR ORAL SUSPENSION CONTAINING LAMOTRIGINE

(71) Applicant: Shanghai Aucta Pharmaceuticals Co., Ltd., Shanghai (CN)

(72) Inventors: Enxian Lu, East Brunswick, NJ (US); Shoufeng Li, Basking Ridge, NJ (US)

(73) Assignee: Shanghai Aucta Pharmaceuticals Co., Ltd., Shanghai (CN)

( * ) Notice: Subject to any disclaimer, the term of this patent is extended or adjusted under 35 U.S.C. 154(b) by 0 days.

(21) Appl. No.: 16/171,914

(22) Filed: Oct. 26, 2018

(65) Prior Publication Data
US 2019/0060237 A1 Feb. 28, 2019

Related U.S. Application Data

(63) Continuation of application No. PCT/US2017/056146, filed on Oct. 11, 2017.

(60) Provisional application No. 62/406,624, filed on Oct. 11, 2016.

(51) Int. Cl.

| A61K 9/16 | (2006.01) |
|---|---|
| A61K 31/53 | (2006.01) |
| A61P 25/00 | (2006.01) |
| A61P 25/24 | (2006.01) |
| A61K 47/10 | (2017.01) |
| A61K 47/36 | (2006.01) |
| A61K 47/02 | (2006.01) |
| A61K 9/00 | (2006.01) |

(52) U.S. Cl.
CPC .......... *A61K 9/1623* (2013.01); *A61K 9/0095* (2013.01); *A61K 9/1611* (2013.01); *A61K 9/1641* (2013.01); *A61K 9/1652* (2013.01); *A61K 31/53* (2013.01); *A61K 47/02* (2013.01); *A61K 47/10* (2013.01); *A61K 47/36* (2013.01); *A61P 25/00* (2018.01); *A61P 25/24* (2018.01)

(58) Field of Classification Search
None
See application file for complete search history.

(56) References Cited

U.S. PATENT DOCUMENTS

| 5,556,639 A | 9/1996 | Fielden |
|---|---|---|
| 5,861,179 A | 1/1999 | Hiskett et al. |
| 6,235,733 B1 * | 5/2001 | Bahal .................. A61K 9/0095 514/230.5 |
| 7,629,331 B2 | 12/2009 | Pipkin et al. |
| 2005/0238724 A1 * | 10/2005 | Aronhime ............ A61K 9/0019 424/489 |

(Continued)

FOREIGN PATENT DOCUMENTS

| GB | 2278057 A | 11/1994 |
|---|---|---|
| WO | 2005051350 A2 | 6/2005 |
| WO | 2007/054975 | 5/2007 |

OTHER PUBLICATIONS

Allen, Loyd V., Ph.D., "Lamotrigine 1 mg/mL Oral Suspension," U.S. Pharmacist (2015); 40(5): 64-65.

(Continued)

*Primary Examiner* — Isis A Ghali
(74) *Attorney, Agent, or Firm* — Fox Rothschild LLP

(57) ABSTRACT

This document discloses a powder formulation of lamotrigine for oral administration. Also disclosed is a suspension of lamotrigine and a method of treating diseases.

18 Claims, 2 Drawing Sheets

(56) References Cited

U.S. PATENT DOCUMENTS

2009/0011037 A1* 1/2009 Pipkin .................. A61K 9/0056
424/499
2010/0016322 A1 1/2010 Nagaraju et al.
2010/0247586 A1* 9/2010 Hugerth .................. A23G 1/32
424/401

OTHER PUBLICATIONS

Zietsman, et al. "Formulation Development and Stability Studies of Aqueous Metronidazole Benzoate Suspensions Containing Various Suspending Agents," Drug Development and Industrial Pharmacy, vol. 33, Issue 2 (Sep. 2007), pp. 191-197.
Third Party Observation filed against International Application No. PCT/US2017/056146 dated Jun. 15, 2018.
Rani et al., "Full Factorial Design in Formulation of Larnotrigine Suspension Using Locust Bean Gum," INternational Journal of Chemical Sciences (2013); 11(2):751-760.

* cited by examiner

POWDER FOR ORAL SUSPENSION CONTAINING LAMOTRIGINE

CROSS-REFERENCE TO RELATED APPLICATIONS

This application is a Continuation of International Application No. PCT/US2017/056146, filed Oct. 11, 2017, which claims priority under 35 U.S.C. § 119(e) to U.S. Provisional Application No. 62/406,624 filed Oct. 11, 2016, the disclosures of which are incorporated herein by reference in their entirety.

FIELD OF THE INVENTION

This patent document discloses a novel formulation of lamotrigine or its pharmaceutically acceptable salt, a method for its preparation and its use in medical therapy.

BACKGROUND

Lamotrigine is marketed in the United States by GlaxoSmithKline LLC, under the trade name Lamictal. Currently, there are three different types of immediate release Lamictal® products approved by US FDA: Lamictal tablets, Lamictal chewable dispersible tablets, and Lamictal orally disintegrating tablets. There are no liquid formulations of lamotrigine commercially available and, as a result, hospital pharmacists are often required to compound liquid formulations using crushed lamotrigine tablets for pediatric patients and patients who cannot swallow tablets. A need exists for an improved formulation of Lamotrigine.

SUMMARY

The powder formulation described herein allows for convenient oral administration of Lamotrigine. The formulation resolved the dose inaccuracy issue due to the precipitation of crushed lamotrigine tablets in a suspension system. Further, the formulation overcomes the hydrate formation problem in aqueous medium and substantially improves the stability and dose accuracy of the medication.

An aspect of this patent document provides a powder formulation suitable for reconstitution with a pharmaceutically acceptable carrier to form a stable suspension oral dosage form. The formulation contains lamotrigine or a pharmaceutically acceptable salt thereof and a suspending agent. The suspending agent is effective for maintaining a sedimentation volume ratio of more than about 0.8 for at least 10 hour after the powder formulation is reconstituted into an aqueous suspension. In some embodiments, the suspending agent reduces the formation of lamotrigine hydrate in the suspension, as compared to equivalent doses of the same lamotrigine in an equivalent suspension but without the suspending agent.

In some embodiments, less than about 5% of the lamotrigine is converted to its hydrate form within about 24 hours after the powder formulation is reconstituted into the suspension. In some embodiments, less than about 0.5% of the lamotrigine or the pharmaceutically acceptable salt thereof decomposes within about 24 hours after the powder formulation is reconstituted into the suspension.

In some embodiments, the lamotrigine or the pharmaceutically acceptable salt thereof and the suspending agent have a ratio ranging from about 10:1 to about 10:5 by weight. In some embodiments, the ratio is about 5:1 by weight.

In some embodiments, the suspending agent is selected from the group consisting of hydrocolloid gum, cellulosic derivative, a polysaccharide, alginate, acrylic acid copolymer, polyvmylpyrrohdone, aluminiummagnesium silicate, and any combination thereof. In some embodiments, the suspending agent is hydrocolloid gum. In some embodiments, the suspending agent is xantham gum.

In some embodiments, the sedimentation volume ratio remains more than about 0.9 within 24 hours after the powder formulation is reconstituted into the suspension. In some embodiments, the suspension is achieved within about 60 seconds after the powder formulation is reconstituted with water. In some embodiments, the suspension is homogeneous.

In some embodiments, the suspension provides an in vitro release of at least about 85% of the lamotrigine in a pH 1 medium after 5 minutes (USP dissolution apparatus 2, in 900 ml of pH 6.8 at 50 rpm). In some embodiments, the powder formulation after being reconstituted into the suspension provides a release of the lamotrigine bioequivalent to Lamictal tablet of the same dose. In some embodiments, the suspension prepared from the powder formulation provides a release of the lamotrigine bioequivalent to a non-suspension dosage form (e.g. Lamictal tablet) which provides a therapeutically effective blood concentration of lamotrigine.

In some embodiments, the lamotrigine or the pharmaceutically acceptable salt thereof has a D90 ranging from about 5 µm to about 150 µm prior to being mixed with the suspending agent.

In some embodiments, the formulation further contains a diluent selected from the group consisting of sucrose, dextrose, mannitiol, sorbitol, maltitol, starch, lactose, microcrystalline cellulose, and any combination thereof in about 10% to about 90% by weight of the powder formulation. In some embodiments, the diluent is sucrose, having a D90 ranging from about 50 µm to about 400 µm prior to being mixed with the suspending agent.

In some embodiments, the formulation further contains a buffering agent selected from the group consisting of sodium citrate, citric acid, fumaric acid, tartaric acid, potassium citrate, sodium bicarbonate, potassium bicarbonate, sodium dihydrogen phosphate, disodium hydrogen phosphate, sodium hydroxide and potassium dihydrogen phosphate.

Another aspect of the invention provides a suspension including lamotrigine or a pharmaceutically acceptable salt thereof or a derivative thereof and a suspending agent. The suspension maintains a sedimentation volume ratio of more than about 0.9 for at least 10 hour after the suspension is prepared. In some embodiments, less than about 5% of the lamotrigine in the suspension is converted to its hydrate form within about 24 hours after the suspension is prepared. The suspension can be prepared from the above described powder formulation by reconstitution or by mixing the necessary components in suitable means as long as the resulting suspension achieves a desirable profile for oral administration.

In some embodiments, the ratio between the lamotrigine (or a pharmaceutically acceptable salt thereof or a derivative thereof) and the suspending agent in the suspension ranges from about 10:1 to about 10:5 by weight. In some embodiments, the ratio is about 5:1 by weight. In some embodiments, the suspending agent is hydrocolloid gum. In some embodiments, the suspending agent is xantham gum.

Another aspect of the patent document provides a method of treating a disease comprising administering the suspension described herein to a subject in need, wherein the disease is selected from the group consisting of seizures, bipolar disorder, depression and neurofibromatosis.

DETAILED DESCRIPTION

Figure 1:
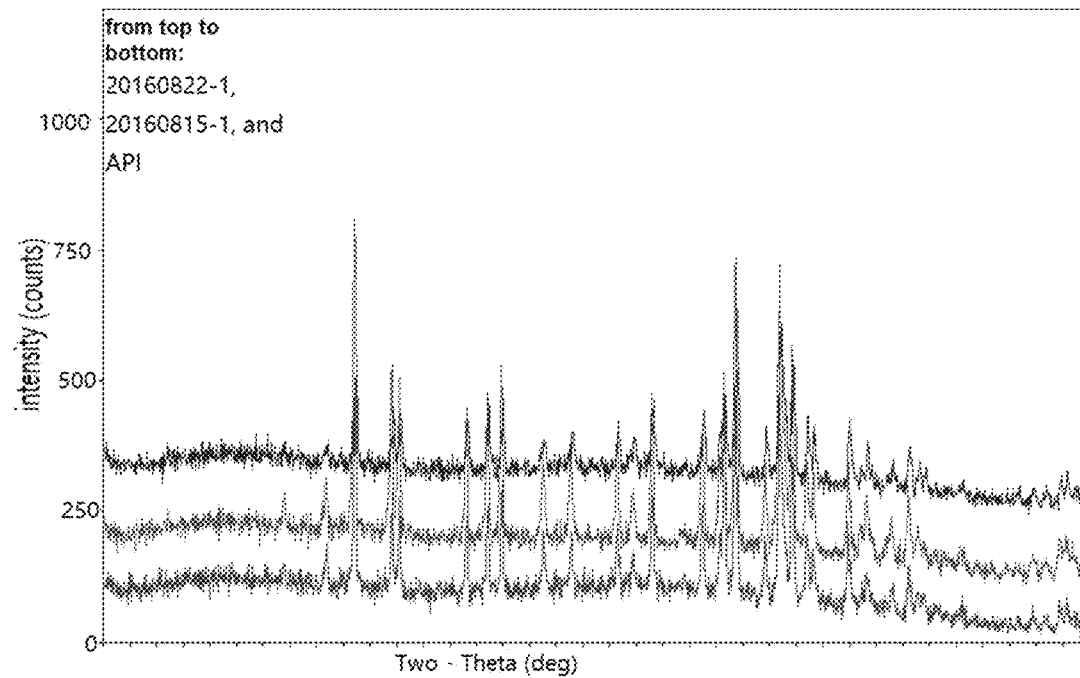
FIG. 1 shows the XRPD results of API, formulation 20160815-1 and formulation 20160822-1 at 2 h. x axis is two theta (deg), y axis is intensity (counts). From top to bottom (20160822-1, 20160815-1 and API).

This document discloses a powder formulation suitable for reconstitution with a pharmaceutically acceptable carrier to form a suspension oral dosage form of lamotrigine. Advantages of the powder formulation and dosage form include prolonged stability, dose titration accuracy and better compliance in comparison with conventional immediate release non-suspension dosage forms.

Lamotrigine is known as 6-(2,3-dichlorophenyl)-1,2,4-triazine-3,5-diamine or 3,5-diamino-6-(2,3-dichlorophenyl)-1,2,4-triazine. Lamotrigine, unless otherwise specified, includes isomers and polymorphs thereof. Lamotrigine is insoluble in water. When crushed lamotrigine tablets are simply added directly into water or other soft food, the compound tends to settle rapidly and cannot be easily redistributed and as such would potentially affect the dose accuracy delivered to a patient. Further, Lamotrigine tends to form hydrate in aqueous media or liquid suspension. Further, Lamotrigine can form a hydrate in an aqueous medium which also affect the dose accuracy and compound stability. The formation of degradant (impurity C) is another issue impacting drug safety.

The powder formulation and suspension dosage form disclosed herein effectively resolved the above issues. After reconstitution, the uniform liquid suspension enables easy and accurate dose titration with an improved taste. Furthermore, the suspending agent in the formulation not only suspends the active ingredient, but also prevents or delays the lamotrigine hydrate formation, which keeps the formulation and dosage consistent for oral administration and thus improves patient compliance. The powder formulation and suspension dosage form described in this patent document are applicable to Lamotrigine as well as salts, isomers, complexes, polymorphs, hydrates, esters and prodrugs thereof.

While the following text may reference or exemplify specific embodiments of a dosage form or a method of manufacturing the dosage from, it is not intended to limit the scope of the dosage form to such particular reference or examples. Various modifications may be made by those skilled in the art, in view of practical and economic considerations, such as the amount of individual excipients and the manufacturing condition.

The articles "a" and "an" as used herein refers to "one or more" or "at least one," unless otherwise indicated. That is, reference to any element or component of an embodiment by the indefinite article "a" or "an" does not exclude the possibility that more than one element or component is present.

The term "about" as used herein refers to the referenced numeric indication plus or minus 10% of that referenced numeric indication.

The term "active ingredient" or "active pharmaceutical ingredient" (API) refers to a compound (e.g. lamotrigine) that can be used for treating a disorder or condition in a subject (e.g., a patient), or for preventing one or more symptoms of such disorder or condition in the subject.

The term "bioequivalence" or "bioequivalent" refers to two formulations, dosage forms, products, or compositions of an active ingredient having biological equivalence. It is generally considered bioequivalent if the 90% Confidence Interval ("CI") of the relative mean Cmax, AUC(0-t) and AUC(0-∞) of the test formulation to reference formulation (i.e., brand product) is within 80.0% to 125.0% in the fasting state of a tested subject.

The term "patient compliance" refers to the degree to which patient correctly follows medical advice.

The term "excipient" refers to any inert substance that may have specific functions to the active ingredient (e.g., swelling agent, controlling-release, osmotic agent). An excipient provides without limitation, bulk, consistency, stability, binding ability, lubrication, disintegrating ability, etc., to the formulation of an active ingredient. A "suspending agent" is a type of excipient. An excipient may function for multiple purposes.

The term "powder" as used herein refers to any composition or formulation which is dry and flowable. Non-limiting examples include granules, flakes, spheroids and other forms which can be readily prepared and mixed with an ingestible liquid to provide a desirable liquid suspension.

The term "wet granulation" refers to a process of using a liquid binder to lightly agglomerate the powder mixture.

The term "release", "released", "releasing", and the like, when used in connection with a pharmaceutical compression or dosage form, refers to the process or the portion of the active ingredient that leaves the dosage form following contact with an aqueous environment. Unless otherwise indicated, the quantity of an active ingredient released from a dosage form is measured by dissolution testing in water as described in this invention. The results of the dissolution testing are reported as % (w/w) released as a function of time or as the release time. In some embodiments, complete release of an active ingredient occurs when at least 90% of the active ingredient has been released from the dosage form.

The term "immediate-release" refers to those which disintegrate rapidly and/or get dissolved to release the medicaments or active ingredient.

The term "Cmax" or "peak plasma exposure", expressed in ng/mL, refers to the point of maximum concentration of drug in plasma.

The term "area under curve (AUC)" or "total plasma exposure", expressed in μg·hr/mL, refers to the total integrated area under plasma level time profile and expresses the total amount of the active ingredient that comes into systemic circulation after administration.

The term "D90" refers to the particle size corresponding to 90% of the cumulative undersize distribution by volume.

The term "pharmaceutically acceptable carrier" refers to an agent or a substance that enable an active ingredient or a composition thereof to be formulated as tablets, pills, dragees, capsules, liquids, gels, syrups, slurries, suspensions and the like, for administration to a subject in need. For example, the carrier can be water or an aqueous solution containing other excipients.

The term "sedimentation volume ratio" or "sedimentation ratio" refers to a ratio of the ultimate volume of sediment (Vu) to the original volume of sediment (VO) before settling.

The term "subject" refers to a mammal, such as an animal or a human. Hence, the methods disclosed herein can be useful in human therapy and veterinary applications. In one embodiment, the subject is an animal. In another embodiment, the subject is a human.

The term "treat" or "treating" refers to attain or attaining a beneficial or desired result, such as a clinical result. In some embodiments, the beneficial or desired result is any one or more of the following: inhibiting or suppressing the onset or development of a condition, reducing the severity of the condition, reducing the number or severity of symptoms associated with the condition, increasing the quality of life of a patient suffering from the condition, decreasing the dose of another medication required to treat the condition, enhancing the effect of another medication a patient is taking for the condition, and prolonging the survival of a patient having the condition.

An aspect of the document provides a powder formulation suitable for reconstitution with a pharmaceutically acceptable carrier to form a stable suspension oral dosage form of lamotrigine. The formulation includes:

lamotrigine, a pharmaceutically acceptable salt, an isomers, a complex, a polymorphs, a hydrate, or an ester thereof;

a suspending agent in an amount ranging from about 0.1% to about 10% w/w based on the total weight of the formulation.

The suspending agent is effective for maintaining a sedimentation volume ratio of more than about 0.9 for at least 10 hours after the powder formulation is reconstituted into a suspension. In addition, the suspending agent reduces the formation of lamotrigine hydrate in the suspension, as compared to equivalent doses of the same lamotrigine in an equivalent suspension but without the suspending agent.

In some embodiments, the pharmaceutically acceptable carrier is water or an aqueous solution containing one or more agents or excipients. The salt of lamotrigine includes for example HCl salt, toluenesulfonic acid (TSA) salt, and methanesulfonic acid (MSA) salt.

The amount of the suspending agent in the formulation can vary depending on factors such as the dosage of lamotrigine and the specific suspending agent. In some embodiments, the suspending agent is present ranging from about 0.5% to about 10%, from about 0.5% to about 10%, from about 0.5% to about 10%, from about 0.5% to about 5%, or from about 0.5% to about 4%.

The suspending agent stabilizes the resulting suspension for an extended period of time after the formulation is reconstituted with for example water or an aqueous solution. In some embodiments, the suspension maintains a sedimentation volume ratio of more than about 0.7, more than about 0.8, or more than about 0.9 for a period of at least about 10 hours, at least about 12 hours, at least about 15 hours, at least about 18 hours, at least about 20 hours, at least about 24 hours, at least about 30 hours, or at least about 48 hours after the formulation is reconstituted.

The sedimentation volume ratio is generally achieved within about 5 minutes, 3 minutes, 2 minutes, 60 seconds, 45 seconds, or 30 seconds after the powder formulation is reconstituted to the suspension. Various mechanical means, such as shaking, swirling, heating, or any combination thereof can be used to promote a uniform suspension.

The suspending agent is able to reduce the formation of lamotrigine hydrate. Exemplary hydrate forms of lamotrigine hydrate are described in U.S. Pat. Nos. 8,486,927 and 7,390,807. The entire disclosure of which including the disclosure on the hydrate forms of lamotrigine is hereby incorporated by reference. In some embodiments, less than about 8%, less than about 5%, less than about 3%, less than about 1%, or less than about 0.5% of the lamotrigine or a pharmaceutically acceptable salt thereof is converted into its hydrate form within about 5 hours, within about 10 hours, within about 12 hours, within about 15 hours, within about 20 hours, within about 24 hours, within about 30 hours, or within about 48 hours after the formulation is reconstituted into a suspension.

The suspending agent also contributes to the stability of the suspension after reconstitution. In some embodiments, less than about 5%, less than about 3%, less than about 1%, less than about 0.5%, less than about 0.2%, or less than about 0.1% of the lamotrigine or a pharmaceutically acceptable salt thereof is decomposed in 10 hours, in about 20 hours, in about 24 hours, in about 2 days, in about 3 days, or in about 1 week after the formulation is reconstituted into a suspension.

The ratio between lamotrigine (or a pharmaceutically acceptable salt thereof) and the suspending agent ranges from about 20:1 to about 1:5 by weight. In some embodiments, the ratio ranges from about 15:1 to about 1:5, from about 10:1 to about 1:5, from about 5:1 to about 1:5, from about 10:1 to about 1:5, from about 10:1 to about 2:1, from about 10:1 to about 1:1, from about 8:1 to about 4:1, from about 6:1 to about 3:1, or from about 6:1 to about 4:1.

Non-limiting examples of the suspending agent include hydrocolloid gums such as xanthan gum, guar gum, locust-bean gum, gum tragacanth, veegum, sodium alginate, carrageenan; cellulosic derivatives such as sodium carboxymethylcellulose, hydroxypropyl cellulose, methyl cellulose, hydroxypropyl methylcellulose; polysaccharides such as starch and pregelatinised starch; alginates such as sodium alginate; acrylic acid copolymers such as carbopols; polyvmylpyrrohdone; aluminiummagnesium silicate; and combinations thereof. In some embodiments, the suspending agent is hydrocolloid gum. In some embodiments, the suspending agent is xantham gum.

The powder formulation after reconstitution into a suspension provides an in vitro release as measured by USP dissolution apparatus 1 or USP dissolution apparatus 2. In some embodiments, at least about 95%, at least about 90%, at least about 85%, at least about 80%, at least about 70, or at least about 60% of the lamotrigine is released in a medium of pH=1 after 5 minutes (USP dissolution apparatus 2, in 900 ml of pH 6.8 at 50 rpm).

The power formulation can also provide a release of lamotrigine bioequivlant to non-suspension formulation of lamotrigine at the same dose. Examples of non-suspension formulation of lamotrigine include Lamictal tablets, Lamictal chewable dispersible tablets, and Lamictal orally disintegrating tablets. In some embodiments, the dose of lamotrigine in the formulation is about 10 mg, 25 mg, 50 mg, 75 mg, 100 mg, 150 mg, 200 mg, 250 mg, 300 mg, or 400 mg.

The lamotrigine or the pharmaceutically acceptable salt thereof or the derivative thereof used for the preparation of the powder formulation has a D90 of less than about 200 μm, less than about 150 μm, less than about 120 μm, less than about 100 μm, less than about 80 μm, less than about 60 μm, less than about 40 μm. In some embodiments, the D90 ranges from about 5 μm to about 150 μm, from about 10 μm to about 120 μm, from about 20 μm to about 100 μm, or from about 30 μm to about 90 μm.

The formulation can contain one or more additional carrier or excipient including for example, surface active agents, sweeteners, lubricants, glidants, diluents, smoothing agents, suspension agents, film forming substances, buffering agents and coating assistants, or a combination thereof. In some embodiments, the formulation further contains a diluent including for example sucrose, dextrose, mannitiol, sorbitol, maltitol, starch, lactose, microcrystalline cellulose, and any combination thereof in about 10% to about 90% by weight of the powder formulation. In some embodiments, the diluent is sucrose. The diluent has a D90 ranging from about 1 μm to about 600 μm, from about 5 μm to about 500 μm, from about 10 μm to about 500 μm, from about 20 μm to about 400 μm, from about 30 μm to about 200 μm, or from about 50 μm to about 180 μm.

In some embodiments, the formulation further contains a buffering agent including for example sodium citrate, citric acid, fumaric acid, tartaric acid, potassium citrate, sodium bicarbonate, potassium bicarbonate, sodium dihydrogen phosphate, disodium hydrogen phosphate, sodium hydroxide and potassium dihydrogen phosphate. The buffer concentration after reconstitution of the powder formulation into a suspension ranges from about 10 mM to about 200 mM, from about 10 mM to about 100 mM, or from about 10 mM to about 50 mM. In some embodiments, the pH of the suspension ranges from about 4 to about 7, from about 5 to about 6 or from about 5.5 to about 6.

In some embodiments, the formulation further contains a sweetener. Non-limiting examples include sucrose, glucose, sorbitol, sucralose, aspartame, saccharin sodium and any other pharmaceutically acceptable sweetener or combination thereof. The amount of the sweetener used in the powder for oral suspension compositions is typically in the range of from about 0.5% to about 90% w/w based on the total weight of the powder formulation.

In some embodiments, the formulation further contains a flavor. Non-limiting examples include grenadine flavor, berry flavor, strawberry flavor, banana flavor, orange flavor and peppermint flavor. The amount of the flavor in the powder for oral suspension is between about 0.1% to about 5% w/w based on the total weight of the powder formulation.

In some embodiments, the formulation further contains a lubricant. Non-limiting examples include silicon dioxide, magnesium stearate, talc and sodium stearyl fumarate. The amount of the lubricant in the powder for oral suspension is between about 0.1% to about 5% w/w based on the total weight of the powder formulation.

Another aspect of this patent document discloses a suspension including (a) lamotrigine or a pharmaceutically acceptable salt thereof or a derivative thereof; and (b) a suspending agent, wherein the suspending agent is effective for maintaining a sedimentation volume ratio of more than about 0.8 for at least 10 hours after the suspension is prepared. In some embodiments, the suspending agent reduces the formation of lamotrigine hydrate in the suspension, as compared to equivalent doses of the same lamotrigine in an equivalent suspension but without the suspending agent.

The ratio between the lamotrigine (or a pharmaceutically acceptable salt thereof or a derivative thereof) and the suspending agent in the suspension is the same as in the above described formulation. In some embodiments, the ratio ranges from about 10:1 to about 10:5 by weight. In some embodiments, the ratio is about 5:1 by weight. The size of the lamotrigine, the suspending agent and other excipients (e.g. diluent, buffering agent) are also as described above. In some embodiments, the suspending agent is hydrocolloid gum. In some embodiments, the suspending agent is xantham gum. Other excipients or carriers can be added to the suspension in any suitable sequence.

The concentration of the lamotrigine (or a pharmaceutically acceptable salt thereof or a derivative thereof) in the suspension is in the range of from about 1 to about 50 mg/ml, from about 1 to about 20 mg/ml, or from about 1 to 15 mg/ml. In some embodiments, the concentration is 5, 8, 10, 15 or 20 mg/ml.

The suspension can be prepared from the above described powder formulation by reconstitution or by mixing the necessary components in suitable means as long as the resulting suspension achieves a desirable profile for oral administration. For example, the suspension can be prepared by adding a pre-calculated amount of water to the above described powder formulation containing suitable dosage of lamotrigine or its salt and thoroughly mix the combined substances. By using a measuring cup or a syringe, a precise dosage can be obtained for oral administration. In exemplary embodiments, the powder formulation can be supplied in vials or bottles for multiple use or in unit dosage sachets for single use. In some embodiments, the powder formulation after reconstitution with water provides a liquid suspension containing 100 mg of lamotrigine per 10 ml of liquid suspension.

The excellent stability of the powder formulation and the suspension allows for accurate dose titration and easy administration. This is especially important for pediatric patients and patients with dysphagia who cannot swallow tablets due to its size.

Another aspect of the patent document provides a method of preparing the above described formulation. The method generally includes mixing the lamotrigine (or a pharmaceutically acceptable salt thereof or a derivative thereof) and the suspending agent. The ratio between the lamotrigine (or a pharmaceutically acceptable salt thereof or a derivative thereof) and the suspending agent in the suspension is the same as in the above described formulation. Additional carriers or excipients described above can also be added in the mixture. Exemplary methods of preparation include dry powder blending, wet granulation, dry granulation by compaction/slugging, spray drying, hot melt extrusion, extrusion spheronization and fluidized bed granulation. As described above, in order to have good uniformity, the active ingredient and all the excipients in the powder formulation should have suitable particle size range and need to pass certain mesh before using, such as mesh 20, 40, 60, 80 or 100.

Another aspect of the patent document provides a method of treating a disease or condition using the powder formulation or the suspension described above. The powder formulation needs to be reconstituted into a suspension. The suspension contains for example, 10 mg/ml of lamotrigine (or a pharmaceutically acceptable salt thereof or a derivative thereof) for oral administration to a subject in need. Examples of the disease or condition include epilepsy, bipolar disorder (e.g. of bipolar I disorder and bipolar II disorder), depression and neurofibromatosis. Examples of epilepsy include tonic-clonic seizures (includes simple partial, complex partial and secondarily generalised seizures). The method can also be used as an adjuvant therapy in partial seizures (focal onset tonic-clonic, atypical absence, myoclonic, and due to Lennox-Gastaut syndrome). Further, it can be used as an alternative therapy for absence seizure and atypical absence, myoclonic, and atonic seizures. Other exemplary applications include treatment of peripheral neuropathy, trigeminal neuralgia, cluster headaches, migraines, and neuropathic pain.

EXAMPLES

Example 1

Two liquid suspension dosage forms, 20160304-1 and 20160323-2, were prepared and are shown in table 1.

TABLE 1

| | liquid suspension | | |
|---|---|---|---|
| Ingredients | 20160304-1 mg (10 ml) | 20160323-2 mg (10 ml) | Function |
| Lamotrigine | 50 | 100 | Drug substance |
| Carrageenan | 40 | 40 | Suspending agent |
| Sodium dihydrate phosphate monohydrate | 30 | 30 | Buffer |
| Polyethylene glycol | 40 | 40 | Wetting agent |
| Sucralose | 10 | 10 | Sweetener |
| Strawberry Flavor | 10 | 10 | Flavor |
| Maltitol | 2000 | 2000 | Sweetener |
| Potassium sorbate | 10 | 10 | Preservative |
| Puried water | 8180 | 8180 | Solvent |

The preparation step of lamotrigine suspension (Batch No.: 20160304-1, 20160323-2) was as following:

1. Dihydrate dihydrogen phosphate, polyethylene glycol, sucralose, strawberry essence, potassium sorbate and maltitol were added successively into 80% of purified water with a stirring speed of 300~500 rpm.
2. Carrageenan was added slowly into the above materials after they are all dissolved, and increase the stirring blade speed gradually and keep the suspension in a spiral when adding carrageenan in which the suspension viscosity increases. Continued stir the suspension for 1 hour at the speed of 500~1000 rpm after the carrageenan was added.
3. Lamotrigine was added slowly into the suspension after carrageenan fully hydration, continue stir the suspension at the speed of 500~1000 rpm for 30 minutes, then fill the suspension into bottles.

The Lamotrigine suspension was transferred into 250 mL PET plastic bottles of pharmaceutical grade, sealed and placed them into the 40° C./RH75% stability chamber for testing their stabilities. The results are shown in Table 2.

TABLE 2

| Lamotrigine suspension accelerated test in 40° C./RH75% | | | | |
|---|---|---|---|---|
| | Impurities C (%) produced under condition of 40° C./RH 75% | | | |
| Batch No. | 2 weeks | 1 month | 2 month | 3 month |
| 20160304-1 | 0.10 | 0.26 | 0.54 | 0.90 |
| 20160323-2 | 0.05 | / | 0.29 | 0.45 |

From table 2, impurity C in batch 20160323-2 (10 mg/ml) was half as that in batch 20160304-1(5 mg/ml) under 40° C./RH75% storage condition. The limit of impurity C in US pharmacopeia is 0.5%. Impurity C of 10 mg/ml suspension (batch 20160304-1) after 2 months storage at 40° C./RH75% is 0.54%, which indicates that the suspension cannot have a two-year shelf life at room temperature. Other antioxidants (such as BHA, BHT) failed to improve suspension stability.

It was observed that after keeping the suspension at room temperature for 3 day, crystals started to form, which impacts the appearance of suspension and re-dispensability, as a result, interfered with dosing accuracy.

The present lamotrigine powder for suspension was developed to improve the chemical and physical stability lamotrigine suspension. The screened suspending agents include Xanthan gum, Carrageenan, Sodium carboxymethyl cellulose, HPMC K4M, Carbomer 934P, as shown in table 3.

TABLE 3

| Screening of Suspending agent | | | | | |
|---|---|---|---|---|---|
| Ingredients | 20160815-1 | 20160815-2 | 20160815-3 | 20160815-4 | 20160815-5 |
| Lamotrigine | 100 | 100 | 100 | 100 | 100 |
| Sucrose | 600 | 600 | 600 | 600 | 600 |
| Xanthan gum | 20 | / | / | / | / |
| Carrageenan | / | 20 | / | / | / |
| Sodium carboxymethyl cellulose | / | / | 20 | / | / |
| HPMC K4M | / | / | / | 20 | / |
| Carbomer 934P | / | / | / | / | 20 |
| Sodium dihydrogen phosphate monohydrate | 30 | 30 | 30 | 30 | 30 |
| Sucralose | 10 | 10 | 10 | 10 | 10 |
| Orange flavor | 6 | 6 | 6 | 6 | 6 |
| Silicon dioxide | 5 | 5 | 5 | 5 | 5 |

The formulation was evaluated through dispersion test (mix the dry powder with same amount of water to form the homogeneous suspension, the shorter mixing time the better) and the sedimentation volume ratio (The sedimentation volume ratio should not less than 0.90).

TABLE 4

| Test results | | | | | |
|---|---|---|---|---|---|
| Items | 20160815-1 | 20160815-2 | 20160815-3 | 20160815-4 | 20160815-5 |
| Dispersion time | ~30 s | >120 s | ~30 s | >120 s | ~60 s |
| Sedimentation ratio | >0.90 | <0.90 | <0.90 | >0.90 | >0.90 |

The test results are shown in Table 4, in which Xanthan gum is the most preferred suspending agent, formulation with xanthan gum has advantage of shorter dispersion time, higher sedimentation volume ratio and the suspended lamotrigine did not settle during an extended period of time.

The present invention also studied the effect of xanthan gum amount on the suspension formation (dispersion time and sedimentation) as shown in Table 5 and 6.

TABLE 5

The formulation with different amount of Xanthan gum

| Ingredients | 20160823-3 | 20160815-1 | 20160829-1 |
|---|---|---|---|
| Lamotrigine | 100 | 100 | 100 |
| Sucrose | 600 | 600 | 600 |
| Xanthan gum | 15 | 20 | 40 |
| Sodium dihydrogen phosphate monohydrate | 30 | 30 | 30 |
| sucralose | 10 | 10 | 10 |
| Orange flavor | 6 | 6 | 6 |
| Silicon dioxide | 5 | 5 | 5 |

TABLE 6

Test results

| Items | 20160823-3 | 20160815-1 | 20160829-1 |
|---|---|---|---|
| Dispersion time | ~20 s | ~30 s | ~60 s |
| Sedimentation volume ratio | >0.90 | >0.90 | >0.90 |

The results show that batch 20160815-1 has the best performance, the ratio of lamotrigine and Xanthan gum is 100:20. When Xanthan gum was too much, it took a long time to form the suspension. If Xanthan gum was too little, sedimentation volume ratio was less than 0.9%. The batch to batch difference of Xanthan gum can also impact the sedimentation ratio if Xanthan gum is too little.

Another formulation of lamotrigine for oral suspension is shown in table 7.

TABLE 7

Formulation of lamotrigine for oral suspension

| | Ingredients | 20160810-1 mg (10 ml) | Function |
|---|---|---|---|
| Internal: | Lamotrigine | 100 | Drug substance |
| | Sucrose | 300 | Diluent, sweetener |
| | Xanthan gum | 20 | Suspending agent |
| External: | Sucrose | 300 | Diluent, sweetener |
| | Sodium dihydrogen phosphate monohydrate, monohydrate | 30 | Buffer |
| | sucralose | 10 | Sweetener |
| | Orange flavor | 6 | Flavor |
| | Silicon dioxide | 5 | Lubricant |

A wet granulation method to prepare batch 20160810-1 is provided as follows:

1. API substance and all the excipients were sieved through 1016 μm screen size mesh by comil.
2. Lamotrigine and internal excipients were weighed into an appropriate wet granulator to mix for 5 minutes, then appropriate amount of water was added to granulator at the shear speed of 300~500 rpm, granulation time for 3~5 minutes;
3. The above wet materials was sieved through a 6350 μm mesh, then dried in a fluidized bed at 50° C. until LOD<2%. The moisture in the wet granulation can be considered to have been removed when LOD<2%.
4. The above dried granules was seived through a 1016 μm mesh, then mix with the external excipients in an appropriate wet granulator at the speed of 20 rpm for 5 minutes.
5. The Lamotrigine powder was packaged for oral suspension with the automatic packing machine.

All excipients were sieved through 1016 μm mesh to break up the lumps in order to facilitate the subsequent mixing since lumps may be formed due to moisture during the storage.

Example 2

A powder formulation for an oral suspension composition or dosage form as set forth below in Table 8 was made as described below. Batch 20160815-1 has the same formulation as that of batch 20160810-1, but was prepared by the dry powder mixing process.

TABLE 8

Composition of batch 20160815-1

| Ingredients | 20160815-1 mg (10 ml) | % (w/w) | Function |
|---|---|---|---|
| Lamotrigine | 100 | 12.97 | Drug substance |
| Sucrose | 600 | 77.82 | Diluent |
| Xanthan gum | 20 | 2.59 | Suspending agent |
| Sodium dihydrogen phosphate monohydrate, monohydrate | 30 | 3.89 | Buffer |
| sucralose | 10 | 1.30 | Sweetener |
| Orange flavor | 6 | 0.78 | Flavor |
| Silicon dioxide | 5 | 0.65 | Lubricant |

The manufacturing process of lamotrigine powder formulation for oral suspension includes:

1. API substance and all the excipients were sieved through 1016 um screen size mesh by comil.
2. All the components were placed in an adequately sized blender and mix for 10 minutes at speed 20 rpm.
3. The powder for oral suspension was packaged using powder automatic packing machine.

The powder for oral suspension was reconstituted to 10 mg/ml liquid suspension with water for oral use. The syringe is used to withdraw the appropriate dosing volume based on patient weight (chart included in the labeling) for delivery in the patient's mouth.

Another lamotrigine powder for oral suspension composition containing no xanthan gum is shown in table 9. This formulation is designed to investigate the function of xanthan gum on delaying the lamotrigine hydrate formation to keep the formulation consistent during the use. The manufacturing process is same as that of batch 20160815-1.

TABLE 9

Composition of batch 20160822-1

| Ingredients | 20160822-1 mg (10 ml) | % (w/w) | Function |
|---|---|---|---|
| Lamotrigine | 100 | 13.32 | Drug substance |
| Sucrose | 600 | 79.89 | Diluent |

TABLE 9-continued

Composition of batch 20160822-1

| Ingredients | 20160822-1 mg (10 ml) | % (w/w) | Function |
| --- | --- | --- | --- |
| Xanthan gum | 0 | 0 | Suspending agent |
| Sodium dihydrogen phosphate monohydrate, monohydrate | 30 | 3.99 | Buffer |
| sucralose | 10 | 1.33 | Sweetener |
| Orange flavor | 6 | 0.80 | Flavor |
| Silicon dioxide | 5 | 0.67 | Lubricant |

Figure 2:
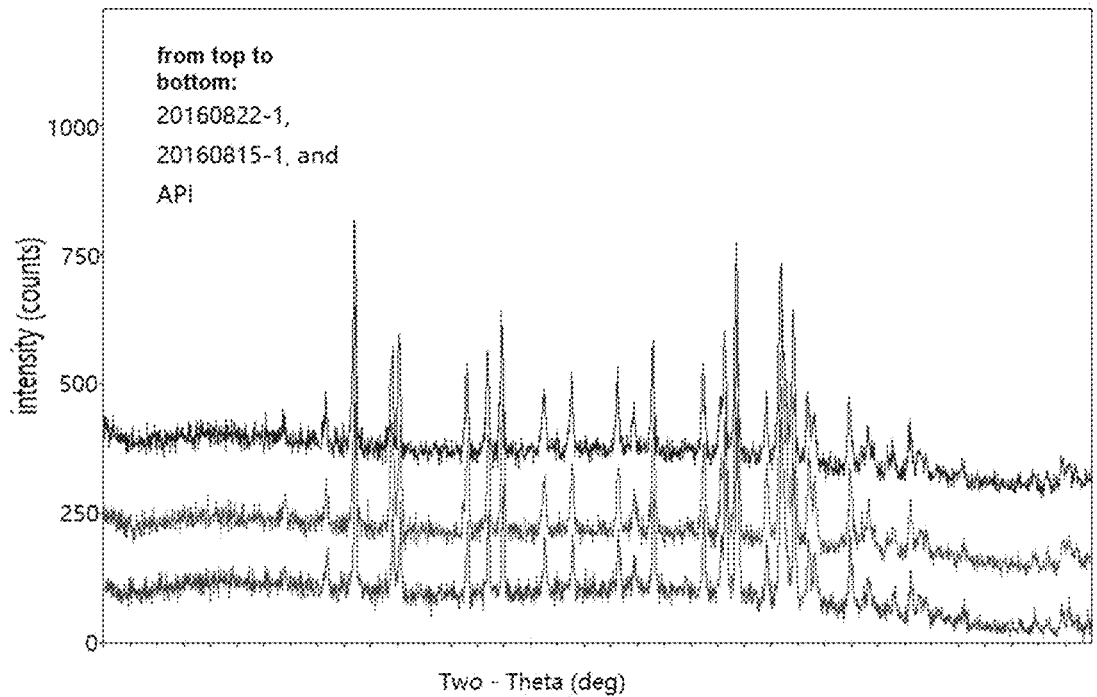
FIG. 2 shows the XRPD results of API, formulation 20160815-1 and formulation 20160822-1 at 4 h. x axis is two theta (deg), y axis is intensity (counts). From top to bottom (20160822-1, 20160815-1 and API).
Figure 3:
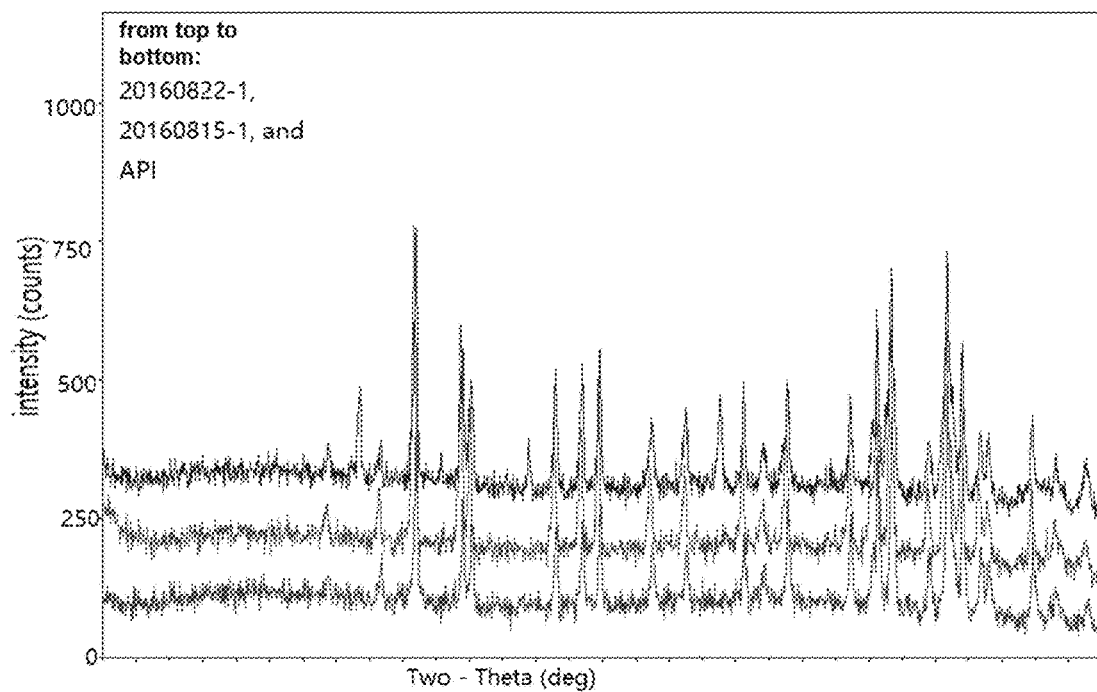
FIG. 3 shows the XRPD results of API, formulation 20160815-1 and formulation 20160822-1 at 8 h. x axis is two theta (deg), y axis is intensity (counts). From top to bottom (20160822-1, 20160815-1 and API).
Figure 4:
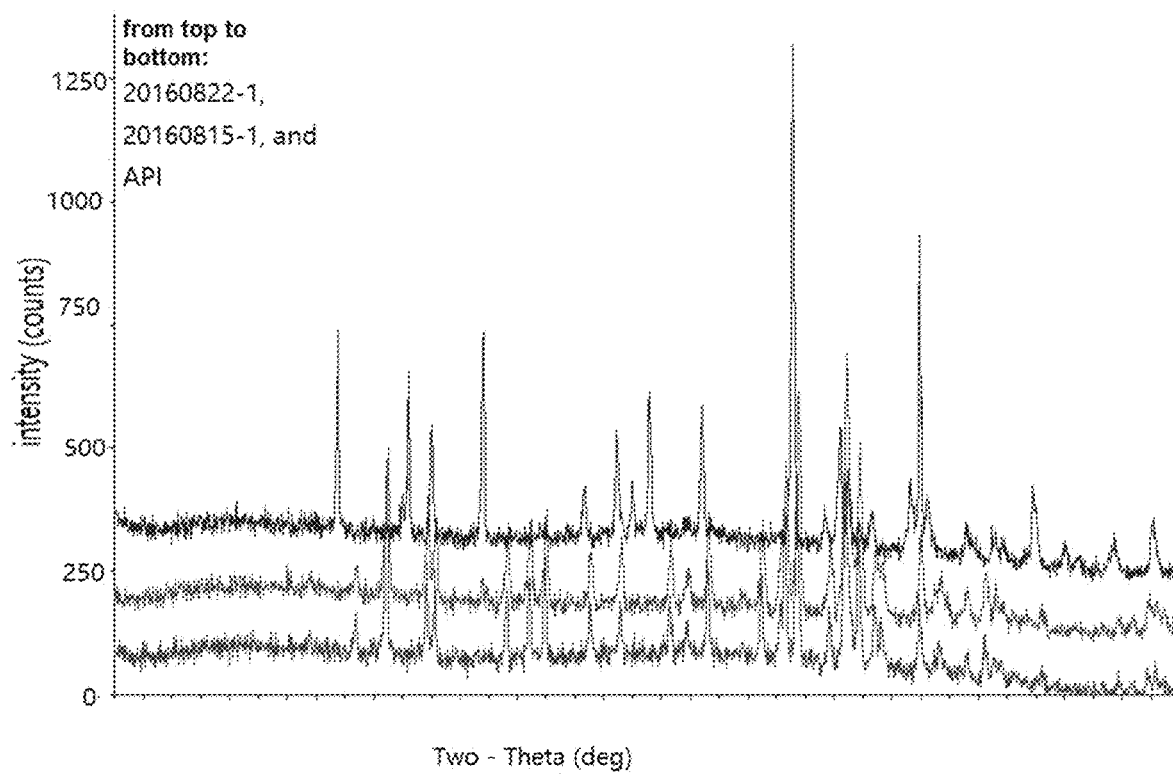
FIG. 4 shows the XRPD results of API, formulation 20160815-1 and formulation 20160822-1 at 24 h. x axis is two theta (deg), y axis is intensity (counts). From top to bottom (20160822-1, 20160815-1 and API).

The formulation 20160815-1 and 20160822-1 were prepared to 10 mg/ml liquid suspension with water respectively, standing for 2, 4, 8 and 24 hour. After centrifuging and drying, the samples were obtained and then analyzed by XRPD instrument, using API as control. The results are depicted in the FIGS. 1-4.

From the XRPD results, drug substance in formulation 20160815-1 containing xanthan gum has the same crystal form with the raw drug substance within 24 h, while the crystal form of drug substance in formulation 20160822-1 containing no xanthan gum changed after 8 h. The new crystal form is hydration of lamotrigine, which is depicted in U.S. Pat. No 8,486,927 B2 and U.S. Pat. No. 7,390,807 B2.

The aforementioned result is surprising since it is generally expected hydrate formation would occur for lamotrigine anhydrate once exposed to water. It has been reported in literature that lamotrigine can easily form hydrate and solvate under various conditions. However, the presence of small amount of suspending agent, in this case, xanthan gum, was found to delay the hydrate formation kinetics.

While the invention has been disclosed in some detail by way of illustration and example for purposes of clarity of understanding, it is apparent to those in the art that various changes may be made and equivalents may be substituted without departing from the true spirit and scope of the invention. Therefore, the description and examples should not be construed as limiting the scope of the invention.

The invention claimed is:

1. A powder formulation suitable for reconstitution with a pharmaceutically acceptable carrier to form a stable suspension oral dosage form comprising a powdered mixture of
lamotrigine or a pharmaceutically acceptable salt thereof in powder form; and
xanthan gum in powder form in an amount ranging from about 2% to about 4% w/w of the powder formulation, further wherein upon reconstituting the powder formulation into an aqueous suspension, said suspension provides a sedimentation volume ratio of more than 0.8 for at least 10 hour.

2. The powder formulation of claim 1, wherein less than 5% of the lamotrigine is converted to its hydrate form within about 24 hours after the powder formulation is reconstituted into the suspension.

3. The powder formulation of claim 1, wherein less than 0.5% of the lamotrigine or the pharmaceutically acceptable salt thereof decomposes within about 24 hours after the powder formulation is reconstituted into the suspension.

4. The powder formulation of claim 1, wherein the lamotrigine or the pharmaceutically acceptable salt thereof and the suspending agent have a ratio ranging from about 10:1 to about 10:5 by weight.

5. The powder formulation of claim 1, wherein the lamotrigine or the pharmaceutically acceptable salt thereof and the suspending agent have a ratio of about 5:1 by weight.

6. The powder formulation of claim 1, wherein the sedimentation volume ratio is more than 0.9 within 24 hours after the powder formulation is reconstituted into the suspension.

7. The powder formulation of claim 1, wherein the suspension is homogeneous and is achieved within about 60 seconds after the powder formulation is reconstituted with water.

8. The powder formulation of claim 1, wherein the suspension provides an in vitro release of at least 85% of the lamotrigine within about 5 minutes under USP dissolution apparatus 2 in 900 ml of pH 6.8 at 50 rpm.

9. The powder formulation of claim 1, wherein the suspension prepared from the powder formulation provides a release of the lamotrigine bioequivalent to Lamictal tablet having the same dose of lamotrigine.

10. The powder formulation of claim 1, wherein the lamotrigine or the pharmaceutically acceptable salt thereof has a D90 ranging from about 20 µm to about 100 µm prior to being mixed with the suspending agent.

11. The powder formulation of claim 10, further comprising a diluent selected from the group consisting of sucrose, dextrose, mannitol, sorbitol, maltitol, starch, lactose, microcrystalline cellulose, and any combination thereof in about 10% to about 90% by weight of the powder formulation.

12. The powder formulation of claim 11, wherein the diluent is sucrose, having a D90 ranging from about 30 µm to about 200 µm prior to being mixed with the suspending agent.

13. The powder formulation of claim 1, further comprising a buffering agent selected from the group consisting of sodium citrate, citric acid, fumaric acid, tartaric acid, potassium citrate, sodium bicarbonate, potassium bicarbonate, sodium dihydrogen phosphate, disodium hydrogen phosphate, sodium hydroxide and potassium dihydrogen phosphate.

14. The powder formulation of claim 1, which is prepared by a process selected from the group consisting of dry powder blending, wet granulation, dry granulation by compaction or slugging, spray drying, hot melt extrusion, extrusion spheronization and fluidized bed granulation.

15. The powder formulation of claim 1, wherein the suspending agent is xanthan gum and the sedimentation volume ratio is more than 0.9 for at least 10 hour after the powder formulation is reconstituted into an aqueous suspension.

16. The powder formulation of claim 1, wherein the suspending agent is effective for preventing the hydrate formation for the lamotrigine for 24 hours after the powder formulation is reconstituted into an aqueous suspension.

17. The powder formulation of claim 10, wherein the D90 of the lamotrigine or the pharmaceutically acceptable salt thereof ranges from about 30 µm to about 90 µm prior to being mixed with the suspending agent.

18. The powder formulation of claim 12, wherein the D90 of the sucrose ranges from about 50 µm to about 180 µm prior to being mixed with the suspending agent.

* * * * *